United States Patent [19]

Matsumura

[11] Patent Number: 4,620,779
[45] Date of Patent: Nov. 4, 1986

[54] OPHTHALMOLOGIC APPARATUS

[75] Inventor: Isao Matsumura, Yokosuka, Japan

[73] Assignee: Canon Kabushiki Kaisha, Tokyo, Japan

[21] Appl. No.: 691,363

[22] Filed: Jan. 14, 1985

Related U.S. Application Data

[63] Continuation-in-part of Ser. No. 509,771, Jun. 30, 1983, abandoned.

[30] Foreign Application Priority Data

Jul. 7, 1982 [JP] Japan ................. 57-119063

[51] Int. Cl.⁴ .............................................. A61B 3/10
[52] U.S. Cl. .................................... 351/211; 351/206
[58] Field of Search ................ 351/205, 206, 211, 237

[56] References Cited

FOREIGN PATENT DOCUMENTS

125321 10/1977 Japan .

Primary Examiner—Rodney B. Bovernick
Assistant Examiner—Paul M. Dzierzynski
Attorney, Agent, or Firm—Fitzpatrick, Cella, Harper & Scinto

[57] ABSTRACT

An ophthalmologic apparatus has a projection system provided with a fixation object capable of being perceived by an examinee, the projection system being for projecting the fixation object upon a desired position on the fundus of an eye to be examined. The apparatus further has an observation system for observing therethrough a portion of the eye to be examined, and a reflecting system disposed between the fixation object and the eye to be examined for directing a light beam emitted from the fixation object to the observation system. In the reflecting system, the light beam emitted from the fixation object and incident on the reflecting system is substantially coincident with a light beam reflected thereby.

5 Claims, 10 Drawing Figures

OPHTHALMOLOGIC APPARATUS

This application is a continuation-in-part of application Ser. No. 509,771 filed June 30, 1983, now abandoned.

BACKGROUND OF THE INVENTION

1. Field of the Invention

This invention relates to an ophthalmologic apparatus, and in particular to an apparatus provided with an object for the fixation of an eye to be examined.

2. Description of the Prior Art

Where the fundus of an eye to be examined is to be observed and photographed, the entire range of the eye fundus cannot be observed and photographed at one time and therefore, the region of interest of the eye fundus must be selected. For this purpose, a fixation object is provided and the line of vision of the eye to be examined is induced, whereby the direction of the field of vision is changed and the interest of region of the eye fundus is selected. Heretofore, as the means for such purpose, a freely movable tiny lamp has been provided on the brow-support or the like for the examinee and the examiner has changed the line of vision of the examinee by moving this lamp. Where the fixation object is thus provided outside the retinal camera and moreover near the brow-support, the operation is cumbersome and observation and photographing are difficult to do. Also, the examinee must see with the eye other than the eye which is examined with respect to the fixation object. Therefore, if the examinee has strabismus, the observer must entirely depend on the sixth sense and thus, the apparatus is very difficult to use. Further, the fixation object is provided near the eye to be examined, and this has led to the disadvantage that where the dominant eye is to be photographed, the line of vision is not exactly fixed.

The present applicant has proposed Japanese Laid-open Patent Application No. 102029/1977 which discloses an apparatus in which the above-noted disadvantage is eliminated. The examinee is caused to perceive the fixation object and the examiner can also confirm the position of the fixation object, but in the specific construction described therein, a fixation object to be perceived by the examiner is provided discretely from the fixation object to be perceived by the examinee. These two fixation objects are operatively associated with each other, and this arrangement requires the provision of a complex device for the operative association. The present applicant has also proposed Japanese Laid-open Patent Application No. 125321/1977, thereby enabling the fixation object to be confirmed also by the examiner without the provision of said device for the operative association. In an example of the prior art shown in FIGS. 1A and 1B of the accompanying drawings, a fixation lamp is presented to the examinee and at the same time, the same fixation lamp is also displayed to the examiner observing the image of the eye fundus.

Figures 1A, 1B:
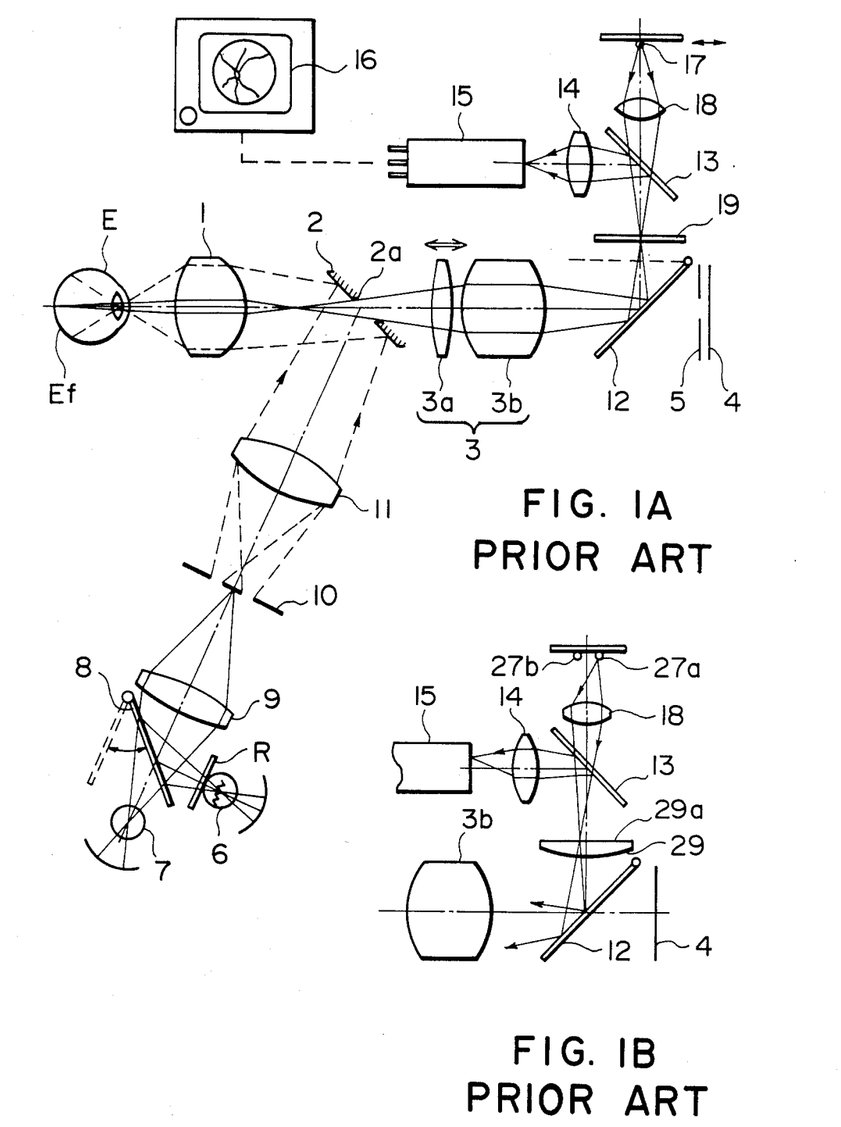
FIGS. 1A and 1B illustrate an example of the prior art.

In FIG. 1A, reference character E designates an eye to be examined, reference character Ef denotes the eye fundus, reference numeral 1 designates an objective lens, reference numeral 2 denotes an apertured mirror, reference character 2a designates an opening in the apertured mirror, reference numeral 3 denotes a picture-taking lens, reference character 3a designates a lens group movable for focusing, and reference character 3b denotes a fixed lens group. The objective lens 1 and the picture-taking lens 3 are disposed in succession from the side of the eye to be examined with their optical axes being coincident with each other, and these constituting a photographing system. Reference numeral 4 designates a film, and reference numeral 5 denotes a shutter. The film 4 and the eye fundus Ef are conjugate with respect to the photographing system.

On the other hand, reference numeral 6 designates a tungsten lamp, reference character R denotes a filter transmitting infrared or near-infrared light, and reference numeral 7 designates a strobo tube such as a xenon discharge tube. The light of the tungsten lamp 6 or the strobo tube 7 is selected by a pivotable mirror 8, which may be retracted out of the light path upon release of a release button (not shown) to pass the emitted strobo light. Reference numeral 9 designates a condenser lens, and reference numeral 10 denotes a well-known ring slit plate. The ring slit plate 10 is conjugate with the illuminating light source 6 or 7 with respect to the condenser lens 9. Designated by 11 is a relay lens for causing the slit image of the ring slit plate to be formed on the apertured mirror 2. The objective lens 1 causes the slit image on the apertured mirror to be re-formed near the pupil of the eye E to be examined. The elements 6 to 11, the apertured mirror 2 and the objective lens 1 together constitute an eye fundus illuminating system. Reference numeral 12 designates an inverting mirror obliquely disposed on the optical axis of the photographing system, and reference numeral 13 denoted a half-mirror having a reflection factor greater than its transmission factor. Reference numeral 14 designates a picture-taking lens, reference numeral 15 denotes a vidicon sensitive also to the wavelength of infrared range, and reference numeral 16 designates a Braun tube for image display. The elements 12 to 15, the objective lens 1 and the picture-taking lens 3 together constitute an eye fundus observing optical system.

Reference numeral 17 designates a display light source which provides the fixation object of the eye to be examined, reference numeral 18 denotes a condenser lens, and reference numeral 19 designates a half-mirror. The mirror surface of the half-mirror 19 is disposed at a position conjugate with the film 4 with respect to the inverting mirror 12, and the fixation light source 17 is provided at a position conjugate with the mirror surface of the half-mirror 19 with respect to the condenser lens 18. Accordingly, the fixation light source 17 is conjugate with the eye fundus with respect to the photographing system 1, 3 and the condenser lens 18.

The fixation light partly reflected by the half-mirror 19 is reflected by the half-mirror 13 and condensed on the image pickup surface of the infrared vidicon 15 by the picture-taking lens 14 and therefore, is displayed on the Braun tube 16.

In FIG. 1B, a field lens 29 is a plano-convex lens having a planar surface as a half-mirror surface 29a which replaces the half-mirror 19 of FIG. 1A.

In FIG. 1A, the fixation light source 17 is movable in a plane perpendicular to the optical axis, but in FIG. 1B, a plurality of fixation light sources 27a and 27b are selectively used. However, in this example of the prior art, as shown in FIG. 1B, the pupil position of the light beam passing from the fixation object to the eye to be examined is not coincident with the pupil position of the light beam reflected by the field lens, that is, the incident light beam is not coincident with the reflected light beam, and therefore, the positional relation between the fixation object and a point on the eye fundus does not commonly depend on the aberration characteristics of the imaging lens. Thus, delicate mutual difference results from aberrations.

SUMMARY OF THE INVENTION

It is an object of the present invention to provide an ophthalmologic apparatus in which a fixation object capable of being perceived by the examinee is also recognized by the examiner.

It is another object of the present invention to provide an ophtalmologic apparatus in which reflecting means for passing therethrough the light from the fixation object to an eye to be examined and partly reflecting said light is provided between the fixation object and the eye to be examined in the optical path, whereby a light beam incident on the reflecting means and a light beam reflected thereby are made substantially coincident with each other.

It is still another object of the present invention to provide an ophthalmologic apparatus in which the reflecting surface of the reflecting means is a dichroic mirror.

The invention will become fully apparent from the following detailed description thereof taken in conjunction with the accompanying drawings.

DESCRIPTION OF THE PREFERRED EMBODIMENTS

Figure 2:
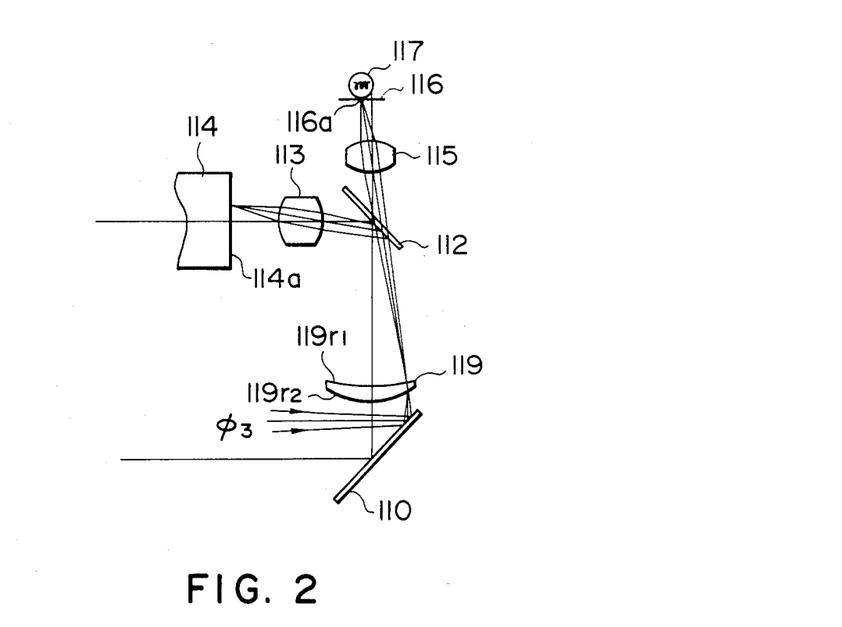
FIG. 2 shows an embodiment of the present invention.
Figure 3:
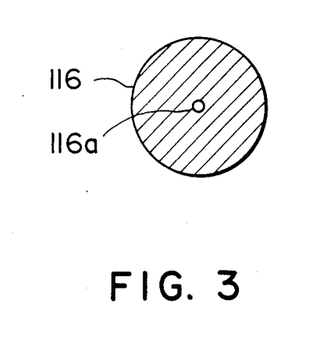
FIG. 3 illustrates a fixation object.

FIG. 2 shows an embodiment of the present invention. This embodiment is an example in which the shape of the reflecting surface is determined so that the pupil position of a light beam passing from a fixation object to an eye to be examined is coincident with the pupil position of a light beam reflected by a field lens 119, that is, light is incident on and reflected by a first surface $119r_1$ perpendicularly thereto. This embodiment has an advantage that any delicate mutual difference resulting from aberrations does not occur because the positional relation between the fixation object and any point on the fundus of the eye commonly depends on the aberration characteristics of an imaging lens 113. That is, the light beam $\phi 3$ from a point on the fundus of the eye to be examined is projected onto an image pickup surface 114a via a quick return mirror 110, a field lens 119, a beam splitter 112 and an imaging lens 113, while the light from the fixation object 116a shown in FIG. 3 which is illuminated by a lamp 117 is imaged on the first surface $119r_1$ of the field lens via a projection lens 115 and the beam splitter 112.

Figure 4:
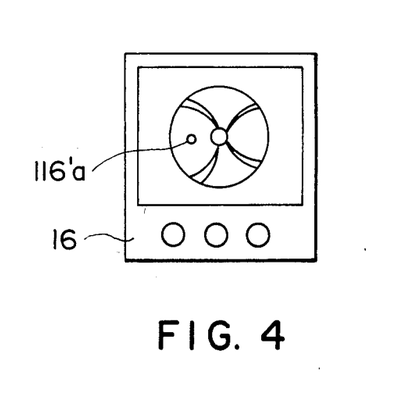
FIG. 4 shows the image of the eye fundus and the image of the fixation object on a monitor.

Thereafter, light from the fixation object travels toward the fundus of the eye via the second surface $119r_2$ of the field lens following a path reverse to that of the light beam $\phi 3$ from the fundus of the eye. On the other hand, the light reflected by the first surface $119r_1$ passes along the original route (identical to the path of the light beam $\phi 3$) and is reflected by the beam splitter 112 and imaged on the image pickup surface 114a by the action of the imaging lens 113. This state is shown in FIG. 4.

Figure 5:
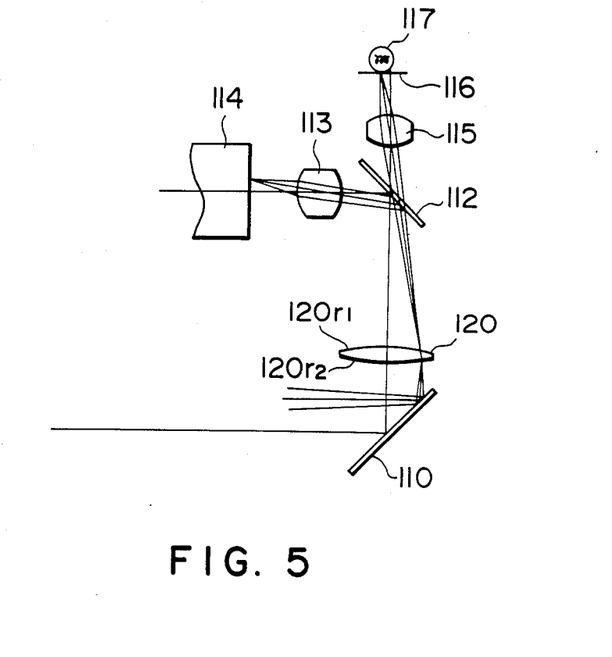
FIG. 5 shows another embodiment of the present invention.

FIG. 5 shows another embodiment which is substantially identical to the above-described embodiment but in which the reflecting surface is a second surface $120r_2$ of a field lens 120. That is, this embodiment is designed such that light is incident on and reflected by the second surface $120r_2$ perpendicularly thereto.

Two embodiments of the present invention have been described above, and one surface of a single lens has been used as the reflecting surface, but the surface reflection of a plurality of optical systems may also be utilized. In the above-described embodiments, the fixation object is provided by a pin-hole formed in a light-intercepting plate, but a light-emitting diode of a small diameter may also be used as the fixation object. It is also possible to selectively turn on one of a plurality of light-emitting diodes disposed in advance, instead of moving the fixation object plate.

Figure 6:
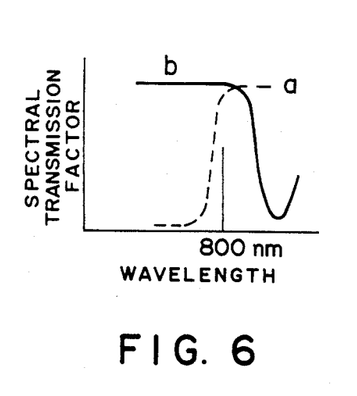
FIGS. 6 and 7 are graphs showing the spectral characteristics of a dichroic mirror.
Figure 7:
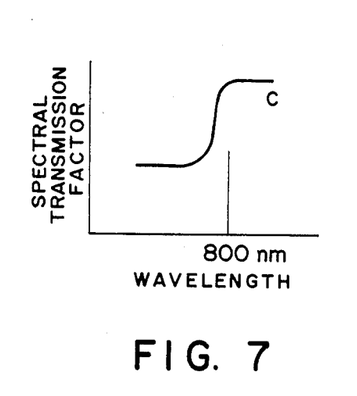

FIGS. 6 and 7 show the spectral characteristics in a case where a dichroic mirror is used as the reflecting surface.

A filter R (the spectral characteristic of which is indicated by curve a in FIG. 6) transmitting infrared light therethrough and intercepting visible light is disposed in the illuminating optical system, and the eye fundus F is illuminated by infrared light. On the other hand, a multi-layer interference film having the spectral characteristic indicated by curve b in FIG. 6, namely, transmitting visible light therethrough and transmitting therethrough light of the infrared range having a relatively short wavelength and reflecting light of the infrared range having a relatively long wavelength is deposited by evaporation on the second surface $r_2$ of the field lens 119. Accordingly, of the light beam coming from the eye fundus, namely, the light of spectral characteristic a, the infrared light of a wavelength shorter than the cut wavelength of spectral characteristic b causes the image of the eye fundus to be formed on the image pickup surface of the image pickup device 114. Also, of the light beam emitted from the pin-hole 116a which is the fixation object, the infrared light of a wavelength longer than the cut wavelength of spectral characteristic b is reflected by the second surface $r_2$ of the field lens 119 and imaged on the image pickup surface. Further, of the light beam emitted from the pin-hole 116a, the visible light is transmitted through the second surface $r_2$ of the field lens 119 and reflected by the quick return mirror 110 and imaged by the imaging lens, whereafter it is subjected to the converging action by an objective lens and imaged on and perceived by the eye fundus. Also, if the second surface $r_2$ of the field lens 119 having the multi-layer interference film thereon is endowed with the spectral characteristic C shown in FIG. 7, namely, the characteristic of transmitting infrared light and half-transmitting light of the visible range, the image of the eye fundus will be picked up by the infrared light and a part of the light from the pin-hole 116a will be directed to the eye fundus and the other part of such light will be directed to the image pickup surface.

Figure 8:
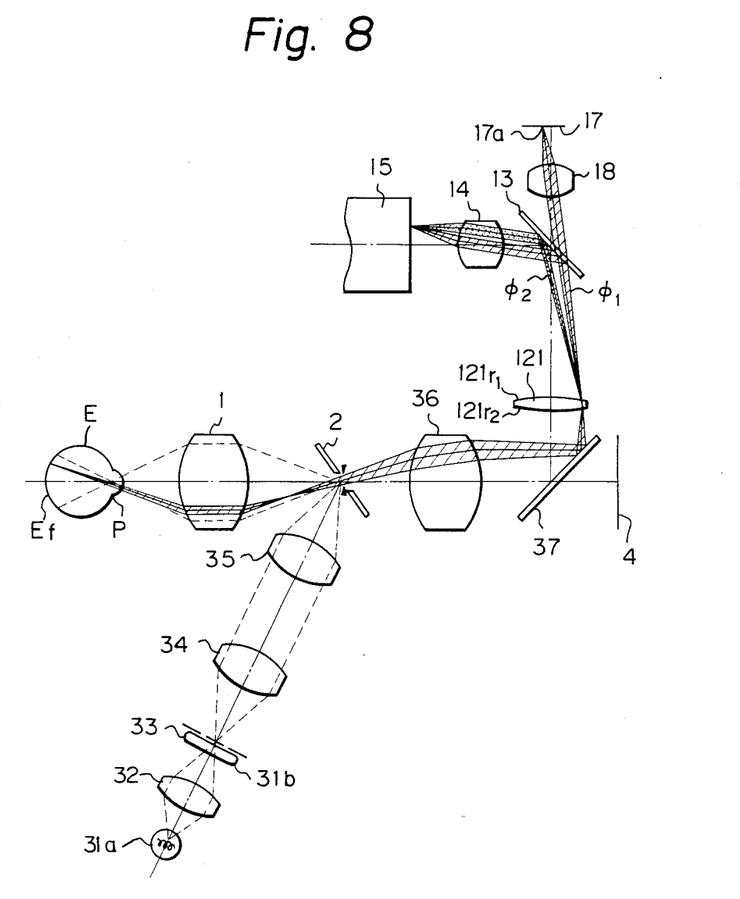
FIG. 8 shows still another embodiment of the present invention.

FIG. 8 shows another embodiment of the present invention where elements described previously are identified by the same reference characters. In FIG. 8, E designates an eye to be examined, Ef denotes the fundus of the eye, and P designates the pupil of the eye. Reference character 31a denotes a light source for observation such as a halogen lamp, and reference character 31b designates a light source for photographing such as a xenon tube. Reference numeral 32 denotes a condenser lens, and reference numeral 33 designates a mask provided with a ring slit. The light source 31a and the mask 33 are conjugate with respect to the condenser lens 32, and the light source 31b is proximate to the mask 33. The light beam passed through the ring slit of the mask 33 is once imaged around the opening of an apertured mirror 2 by the action of relay lenses 34 and 35, whereafter it is reflected by the apertured mirror, enters an objective lens 1 from the opposite direction, and is again imaged near the pupil P of the eye E to be examined. Thereafter, this light beam illuminates the eye funds Ef. The light from the eye fundus Ef again passes through the pupil and is imaged by the objective lens 1, whereafter it passes through the opening of the apertured mirror 2 and is subjected to the imaging action by a photo-taking lens 36, and is reflected by a quick return mirror 37. This light beam $\phi_1$ is imaged on the second surface $121r_2$ of a field lens 121 located at a position equivalent to a film 4, whereafter it is reflected by a beam splitter 13 which is a half-mirror and is subjected to the imaging action by an imaging lens 14. Thereafter the light beam $\phi_1$ is imaged on the image pickup surface of an image pickup device 15 such as a vidicon tube or the like. On the other hand, consider a light transmitted through the beam splitter 13. If a target plate 17 provided with a pin-hole (target) 17a is movably supported at a position whereat this light is imaged by a projection lens 18 and an illuminating lamp is disposed rearwardly of the target plate, the light beam passed through the pin-hole 17a follows the above-described optical path and arrives at a corresponding position on the eye fundus Ef and is perceived by the examinee. Also, if the target plate 17 is moved in a plane, the projected light from the target can be made to enter a desired position on the eye fundus Ef and, therefore, the examinee's line of sight can be suitably arranged.

If the second surface $121r_2$ of the field lens 121 is subjected to some reflection treatment, the light beam passed through the pin-hole 17a and subjected to the converging action by the projection lens 18 will be transmitted through the beam splitter 13 and part of the light beam will be reflected back by the second surface $121r_2$ of the field lens 121 when it is once imaged on the second surface $121r_2$. If the magnitudes and combination of the radii of curvature of the first surface $121r_1$ and the second surface $121r_2$ of the field lens 121 are properly selected, the reflected light beam $\phi_2$ will efficiently enter the imaging lens 14 and can be imaged on the image-receiving surface of the image pickup device 15. That is, the exit pupil of the projection lens 18 and the entrance pupil of the imaging lens 14 are made substantially conjugate with respect to the second surface $121r_2$ of the field lens 121.

Figure 9:
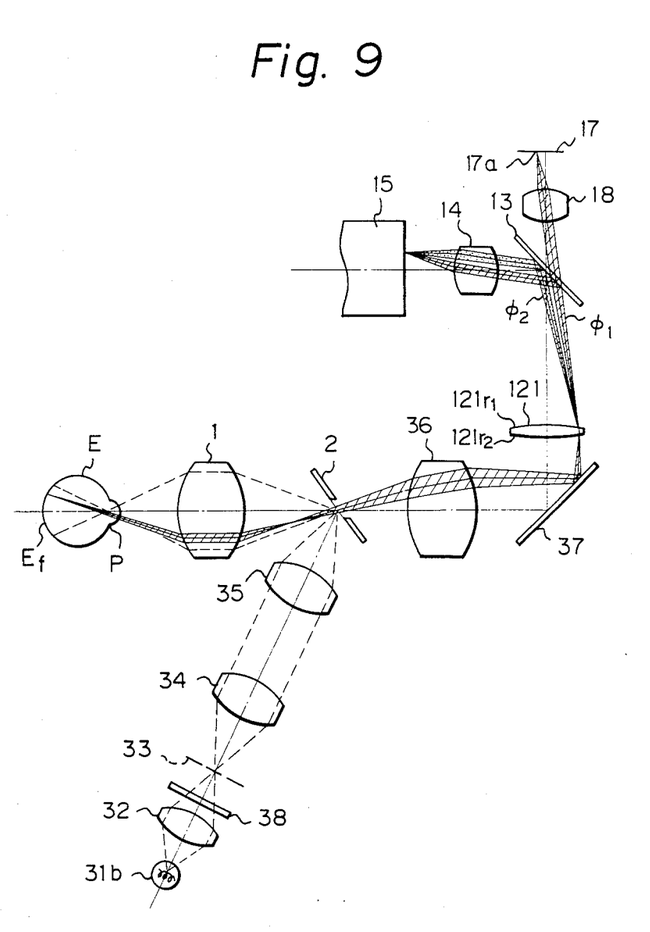
FIG. 9 shows a modification of the embodiment shown in FIG. 8.

FIG. 9 shows a modification of the embodiment of FIG. 8. In this modification, a filter 38 (having the spectral characteristic (a) shown in FIG. 6) transmitting infrared light therethrough and intercepting visible light is disposed in the illuminating optical system and infrared light illuminates the eye fundus Ef. On the other hand, a multi-layer interference film having the spectral characteristic (b) shown in FIG. 6, that is, transmitting visible light therethrough and transmitting a relatively short wavelength infrared light therethrough and reflecting relatively long wavelength infrared light, is deposited by evaporation on the second surface $121r_2$ of the field lens 121. Accordingly, of the light of the spectral characteristic (a) shown in FIG. 6 coming from the eye fundus, the infrared light of a wavelength shorter than the cut wavelength of the spectral characteristic (b) is imaged on the image pickup surface of the image pickup device 15. Also, of the light beam passed through the pin-hole 17a which is a target, the infrared light of wavelength longer than the cut wavelength of the spectral characteristic (b) shown in FIG. 6 is reflected by the second surface $121r_2$ of the field lens 121 and is imaged on the image pickup surface. Further, of the light beam passed through the pin-hole 17a, the visible light is transmitted through the second surface $121r_2$ of the field lens 121, is reflected by the quick return mirror 37, and is imaged by the imaging lens 36, whereafter it is subjected to the converging action of the objective lens 1, is imaged on the eye fundus Ef, and is perceived by the examinee. Also, if the filter 38 has the spectral characteristic (c) shown in FIG. 7, i.e., the characteristic of transmitting infrared light therethrough and semi-transmitting visible light, the image of the eye fundus will be picked up by the infrared light and part of the light from the pin-hole 17a will travel toward the eye fundus and the other part of said light will travel toward the image pickup surface.

According to the present invention described above, the image of the fixation object can be efficiently directed to the observation system and therefore, confirmation of the positional correspondence to the eye to be examined can be accomplished and induction of the line of vision can also accomplished accurately.

What I claim is:
1. An ophthalmologic apparatus comprising:
an illuminating system for illuminating an eye to be examined;
an observation optical system;
observation means for observing the fundus of the eye to be examined through said observation optical system;
a field lens having a partially-reflective curved lens surface, said lens surface being disposed at a position conjugate with the fundus of the eye to be examined with respect to said observation optical system;
light dividing means provided between said field lens and said observation means for forming a first optical path directed toward said observation means and a second optical path branching off from said first optical path;
a target provided in said second optical path and being capable of being perceived by the eye to be examined;
a first lens for imaging said target in the vicinity of said curved lens surface of said field lens; and
a second lens provided in said first optical path for focusing on said observation means a light beam which is incident on said curved lens surface from said target through said first lens and then is reflected by said curved lens surface, an entrance pupil of said second lens being at a position conjugate with an exit pupil of said first lens with respect to said curved lens surface so that any effective light beam from said target through said first lens, including an off-optical axis light beam, is directed back toward said observation means through said second lens.

2. An opthalmologic apparatus comprising:

illuminating means for illuminating an eye to be examined;

an observation optical system;

observation means for observing the fundus of the eye, illuminated by said illuminating means, through said observation optical system;

a field lens having a partially-reflective curved lens surface, said lens surface being disposed at a position conjugate with the fundus of the eye to be examined with respect to said observation optical system;

light dividing means provided between said field lens and said observation means for forming a first optical path directed toward said observation means and a second optical path branching off from said first optical path;

a target provided in said second optical path and being capable of being perceived by the eye to be examined;

a first lens for imaging said target in the vicinity of said curved lens surface of said field lens; and a second lens provided in said first optical path for focusing on said observation means a light beam which is incident on said curved lens surface from said target through said first lens and then is reflected by said curved lens surface, said curved lens surface being shaped so that the light beam incident on said curved lens surface from said target is substantially coincident with the light beam reflected by said curved lens surface after being incident on said curved lens surface from said target, thereby causing any effective light beam from said target through said first lens, including an off-optical axis light beam, to be directed back toward said observation means through said second lens.

3. An opthalmologic apparatus according to claim 2, wherein said partially-reflective curved lens surface is a dichroic mirror.

4. An ophthalmologic apparatus according to claim 3, wherein said dichroic mirror partially transmits visible light and transmits near infrared light therethrough.

5. An ophthalmologic apparatus according to claim 3, wherein said dichroic mirror transmits visible light and near infrared light near the visible light range, and reflects near infrared light far from the visible light range.

* * * * *

UNITED STATES PATENT AND TRADEMARK OFFICE
CERTIFICATE OF CORRECTION

PATENT NO. : 4,620,779
DATED : November 4, 1986
INVENTOR(S) : ISAO MATSUMURA

It is certified that error appears in the above-identified patent and that said Letters Patent is hereby corrected as shown below:

COLUMN 1

Line 21, "interest of region" should read --region of interest--.

COLUMN 5

Line 19, "funds" should read --fundus--.

COLUMN 6

Line 36, "accomplished" should read --be accomplished--.

Signed and Sealed this

Twenty-fourth Day of February, 1987

Attest:

DONALD J. QUIGG

Attesting Officer      Commissioner of Patents and Trademarks